(12) United States Patent
Kim

(10) Patent No.: US 9,233,183 B2
(45) Date of Patent: Jan. 12, 2016

(54) DEVICE FOR INDOOR AIR PURIFICATION AND STERILIZATION

(76) Inventor: Bu-yeol Kim, Seoul (KR)

( * ) Notice: Subject to any disclaimer, the term of this patent is extended or adjusted under 35 U.S.C. 154(b) by 0 days.

(21) Appl. No.: 13/502,371

(22) PCT Filed: Oct. 11, 2010

(86) PCT No.: PCT/KR2010/006924
§ 371 (c)(1),
(2), (4) Date: Apr. 16, 2012

(87) PCT Pub. No.: WO2011/046325
PCT Pub. Date: Apr. 21, 2011

(65) Prior Publication Data
US 2012/0207647 A1     Aug. 16, 2012

(30) Foreign Application Priority Data
Oct. 16, 2009 (KR) .................. 10-2009-0098693

(51) Int. Cl.
| A61L 9/00   | (2006.01) |
| A61L 9/014  | (2006.01) |
| A61L 9/03   | (2006.01) |
| A61L 9/22   | (2006.01) |
| A61L 9/20   | (2006.01) |
| A01N 1/02   | (2006.01) |
| B01D 35/06  | (2006.01) |
| B03C 1/00   | (2006.01) |
| B03C 3/00   | (2006.01) |
| B03C 3/017  | (2006.01) |
| B03C 3/155  | (2006.01) |
| F02C 7/05   | (2006.01) |
| F24F 13/28  | (2006.01) |

(52) U.S. Cl.
CPC ................ *A61L 9/00* (2013.01); *A01N 1/0294* (2013.01); *A61L 9/014* (2013.01); *A61L 9/03* (2013.01); *A61L 9/205* (2013.01); *A61L 9/22* (2013.01); *B01D 35/06* (2013.01); *B03C 1/002* (2013.01); *B03C 3/00* (2013.01); *B03C 3/017* (2013.01); *B03C 3/155* (2013.01); *F02C 7/05* (2013.01); *F24F 13/28* (2013.01)

(58) Field of Classification Search
CPC ............ A61L 9/00; A61L 9/014; A61L 9/03; A61L 9/22; A61L 9/205; A01N 1/0294; B01D 35/06; B03C 1/002; B03C 3/00; B03C 3/017; B03C 3/155; F02C 7/05; F24F 13/28
USPC ......... 422/22, 121, 123–124, 186.04, 186.07, 422/305–306
See application file for complete search history.

(56) References Cited

U.S. PATENT DOCUMENTS

| 6,635,156 B1 | 10/2003 | Dodonov et al. |
| 2002/0076370 A1 * | 6/2002 | Wong et al. .............. 422/186.12 |
| 2006/0221536 A1 | 10/2006 | Goto |

OTHER PUBLICATIONS

International Search Report for PCT/KR2010/006924 Mailed on July 27, 2011.

*Primary Examiner* — Monzer R Chorbaji
(74) *Attorney, Agent, or Firm* — Revolution IP, PLLC

(57) ABSTRACT

The present invention relates to a device for indoor air purification and sterilization which excites indoor air by arc discharge to decompose bad odor and sterilize air, wherein an excited state is maintained by applying a magnetic field and the contact time between molecules activated by arc and pollutants is extended, thereby improving air purification and sterilization effects, and the noise generated by arc discharge is reduced by a silencer and ozone and static electricity are removed by a filter which removes ozone and a metal filter for removing static electricity, respectively, thereby enabling very suitable configuration for indoor air purification and sterilization.

4 Claims, 3 Drawing Sheets

DEVICE FOR INDOOR AIR PURIFICATION AND STERILIZATION

RELATED APPLICATIONS

This application is a 371 application of International Application No. PCT/KR2010/006924, filed Oct. 11, 2010, which in turn claims priority from Korean Patent Application No. 10-2009-0098693, filed Oct. 16, 2009, each of which is incorporated herein by reference in its entirety.

TECHNICAL FIELD

The present invention relates to a device for decomposing contamination substances and bad smells and sterilizing the same by filtering contaminated indoor air by means of an arc discharge, and in particular a device for indoor air purification and sterilization which is characterized in that contaminated substances and bad smell are decomposed by filtering indoor air by way of an arc discharge and sterilizing the same, and an excited state is maintained by generating a magnetic field, and a contact duration time between arc active molecules and contaminated substances can be prolonged, thus significantly enhancing air purification and sterilization efficiencies, and the noises occurring during an arc discharge are reduced by a muffler, and ozone and static electricity are eliminated using an ozone elimination filter and a static electricity elimination metallic filter, thus being most well adapted to an indoor air purification and sterilization.

BACKGROUND ART

Since the 1970s, buildings built in an airtight structure and an energy saving structure in an attempt to save energy and enhance energy efficacy continue to increase in a variety of industries. A variety of ways are widely under ways for an airtight construction of buildings and energy consumption reduction for the purpose of facilitating a carbon emission restriction and an emission trading due to a high oil price and a depression in economy and a framework convention of a climate change since the 2008s. For these reasons, the quality of indoor air of a building is fast being worsened.

The problems of indoor environments might be directed to a phenomenon of contaminating indoor environments as various contamination substances generating due to the activities of human beings are directly emitted into the indoor space, namely, it might be the problems occurring due to the indoor contamination.

A variety of physically, chemically and biologically different contamination substances might exist in the indoor air. Since the above mentioned contamination substances come from combined discharge sources such as the input of external air, cigarette smoke, heater, oven, cooking utensils, cement, washing agent, construction materials, paint, etc., the discharge amounts of each source are of very deviated differences depending on the kinds of contamination substances.

For example, the indoor air quality of a department store in Seoul was measured. As a result of the measurement, $CO_2$ was 779 PPM, $NO_2$ was 40 PPM, HCHO was 0.16 PPB, TSP was 0.023 μg/m$^2$, and in terms of microorganism, fungus was 297 CFu/M$^3$, and the total bacteria was 1622 CFu/m$^3$. In addition, the offices located in industrial factories had a variety of harmful bad smell substances such as $NH_3$, $H_2S$, $C_6H_6$ etc. now that various process gases were introduced into the offices, the substances of which were reported to cause health disorders.

In order to resolve the above problems, a method is provided to eliminate micro dusts using an air purification machine with a plurality of filter units. In recent years, it is being attempted to deodorize and sterilize using an air purifier which is equipped with a deodorizing filter with carbon or something in addition to a micro dust elimination filter, and an antibacterial filter or something equipped with a silver nano carbon; however due to the structural characteristics of an indoor type air purification machine, deodorizing and sterilizing effects are bad since it is not easy to install enough a carbon and a silver nano carbon in the filters, and it is needed to periodically exchange the filters.

As a conventional method for eliminating bad smells in the air generally used in the industry, there are a washing tower for spraying washing water, an adsorption tower for eliminating bad smells by forcing to pass through filled carbon layers, and an incineration method. The above apparatuses are hard to be made in a compact size for the purpose of being used for indoor air purification due to the natural characteristics of the apparatuses. In addition, the washing tower is good only at eliminating bad smells from a hydrophilic substance, and the adsorption tower is needed to periodically exchange the carbon which is an adsorption material. The incineration method is needed to burn LNG, so it is hard to actually adapt for the purpose of indoor air purification.

In addition, as a method for sterilizing the bacteria in the contaminated air, there is disclosed an apparatus sterilizing bacteria by spraying, into the contaminated air, ozone water produced as ozone is dissolved in water; however since an ozone generator, an ozone dissolver and a discharged ozone treatment apparatus are necessarily needed, so the apparatus becomes complicated and is expensive. In particular, if the ozone discharged is not treated in a proper way, it might be discharged into the indoor space, so the respiratory organs of the people staying in the indoor space might be damaged. If ozone is discharged into the air, optical chemical smog might be formed, thus contaminating the air environment.

In terms of an apparatus and a method for purifying the air using ozone like the above mentioned methods, there is a Korean utility model registration publication number 0434060 (Title of the design: Advanced air deodorizor and process based on ozone (water), plasma and catalyst) discloses a deodorizer and its method which is characterized in that an ozone pump is pumped for an elimination of bad smell into an ozone water tank, and it is sprayed via a spraying nozzle, thus purifying the air. The moisture is eliminated using demister and is discharged. However, the deodorizer is directed to a construction purifying the air by spraying ozone water into the air which rises up in the interior of the purification container. In this case, the purification container should be inevitably larger, namely, it is impossible to make it smaller, so such the above deodorizer is used for only the purpose of industry, not for the purpose of a home or an indoor space.

The Korean patent publication number 2008-96973 (Title of the invention: Apparatus for spraying ozone fog) discloses an apparatus for spraying ozone fog which is directed to enhancing an air purification performance in such a way to spray air along with ozone and water. The apparatus for spraying ozone fog is based on a method for directly spraying ozone into the air, so the humidity of the indoor space increases. Since the ozone is not dissolved in water, but ozone and water are separately sprayed into the air, it cannot be used in a space with a high humidity. It is basically designed to spray directly toward a person, a thing, an apparatus or something, it is uneasy to use. In addition, severe harmfulness might occur due to the ozone which is directly sprayed.

The Korean utility model registration publication number 0428872 (Title of the invention: The air cleaner with disinfection and sterilization for in the room which possesses an ozone water making device) is directed to an air cleaner with disinfection and sterilization for in a room which possesses an ozone water making device which is characterized in that when sterilizing food materials and various utensils with ozone water, an inclusion concentration and an inclusion time of ozone water are made to be enough while continuously supplying ozone water, and the apparatus can be movably installed at an indoor space, thus purifying indoor air and sterilizing the whole indoor spaces; however the above air cleaner with disinfection and sterilization for in the room is directed to directly discharging ozone gas into the indoor air, so the discharged ozone gas might directly damage human body.

A small size apparatus designed to purify the indoor space using an arc discharge occurring from a plurality of spaced-apart electrode is widely being developed for the purpose of the use in the indoor space by resolving the above mentioned problems.

The Korea patent publication number 2005-102600 (Title of the invention: Plasma odor and germ remover) is directed to a plasma odor and germ remover which is characterized in that contaminated air containing a variety of harmful substances such as various volatile organic compounds and smell and bacteria is in real time oxidized and decomposed with the aid of sliding arc plasma produced from a plurality of electrodes and plasma oxidation ion produced from a photocatalyst filter. The above-mentioned plasma odor and germ remover is theoretically possible to remove contaminated substances with the aid of a sliding arc plasma by way of an arc discharge and a plasma oxidation ion produced from a photocatalyst filter; however since the exited state of contaminated air caused by means of an arc discharge ends within a very short time, the oxidation and decomposition efficiencies of the harmful substances contained in the contaminated air are very low, and there are not provided a certain means for shielding electromagnetic waves produced during arc discharge and a certain means for removing ozone, so the produced electromagnetic waves and ozone might provide human bodies with serious bad effects, whereby the above plasma odor and germ remover is not well applied to the purifications of indoor air.

The Korean patent publication number 2008-4018 (Title of the invention: An air purification system of a cattle shed, removing device ammonium-nitrate of ozonizer) is directed to an air purification system of a cattle shed which is characterized in that there are provided a pair of electrode plates generating ozone by way of arc discharge and an ozone generation means containing an oxidation catalyst layer which facilitates an oxidation operation, thus oxidizing and removing bad smells and harmful gases with the aid of ozone produced by means of the ozone generation means. The above mentioned air purification system is characterized in that since the excited state of the contaminated air, which excited state occurs by means of arc discharge, ends within a very short time, so the oxidation and decomposition efficiency of the harmful substances contained in the contaminated air is very low, and since there are not provided a means for shielding the electromagnetic waves generating during the arc discharge and a means for reducing noises, the electromagnetic waves and noises are harmful to human bodies, and since the ozone generating during the arc discharge is discharged into the air, it provides bad effects to environment.

The Korean patent registration publication number 10-0840935 (Title of the invention: Plasma and bio filter hybrid gas cleaning system) is directed to a plasma and bio filter hybrid gas cleaning system which is characterized in that a harmful gas decomposition performance is enhanced by concurrently supplying water and harmful gas to a plasma reaction part, and a harmful gas purification function of microorganism is enhanced by uniformly supplying micro water particles and oxygen to a bio filter with the aid of a fluid nozzle spray and plasma discharge. The above mentioned plasma and bio filter hybrid gas cleaning system is characterized in that the excited state of contaminated air produced by means of arc discharge ends within a very short time, so the oxidation and decomposition efficiencies of harmful substances contained in the contaminated air are very low, and since there are not provided a means for shielding electromagnetic waves produced during arc discharge, a means for eliminating ozone, and a means for reducing noises, whereby the electromagnetic waves, ozone and noise might seriously affect human body. So, it is not well applied to the purification of the indoor air.

In conclusion, a conventional small size apparatus for purifying indoor air using arc discharge is characterized in that since the excited state of contaminated air produced by means of arc discharge ends within a very short time, the oxidation and decomposition efficiencies of the harmful substances contained in the contaminated air are very low, and since there are not provided a means for shielding electromagnetic waves produced during arc discharge, a means for eliminating ozone, and a means for reducing noises, whereby the electromagnetic waves, ozone and noise might seriously affect human body. So, it is not well applied to the purification of the indoor air.

DISCLOSURE OF INVENTION

Accordingly, the present invention is made to resolve the problems encountered in the conventional art. It is an object of the present invention to provide an a device for indoor air purification and sterilization which is characterized in that contaminated substances and bad smells are decomposed and sterilized by exciting contaminated indoor air by means of arc discharge, and the excited state is maintained by applying magnetic field, and the air purification and sterilization efficiencies can be significantly enhanced by extending the contact duration time between the arc-activated molecular and contaminated substances, and the noises produced due to arc discharge is reduced by a muffler, and ozone and static electricity are removed by an ozone elimination filter and a static electricity elimination metallic filter, respectively, so the present invention is well adapted to the purification and sterilization of the indoor air.

To achieve the above objects, there is provided a device for indoor air purification and sterilization, comprising a suction tube which is disposed at one side of a housing; a dust elimination pretreatment filter which is formed at the suction tube; an air pump or air suction fan which is disposed near the dust elimination pretreatment filter; an arc discharge part which has an arc discharge unit for exciting the contaminated gases sucked by means of the air pump, a titanium dioxide ($TiO_2$) formed at an inner surface of a discharge support tube accommodating the arc discharge unit, and an electromagnetic wave shielding layer formed at an outer surface; a magnetic field process part which has an induction coil for the purpose of maintaining an excited state by applying a magnetic field to the gas from the arc discharge part and a magnetic layer formed at an inner surface of the induction coil support tube accommodating the induction coil, with the outer surface of the magnetic field process part being covered by means of permanent magnets; a muffler which is connected with the magnetic field process part and has a sound absorption material on its inner surface or has a plurality of noise reduction baffles; an ozone elimination filter which is disposed in the interior of an exhaust tube connected with the muffler and is configured in such a manner that at least one ozone decomposition catalyst selected from the group consisting of $MnO_2$, CuO and zeolite is loaded at a porous carrier; and a static electricity elimination metallic filter which is disposed near the ozone elimination filter and is made from copper or a stainless steel material and is grounded.

ADVANTAGEOUS EFFECTS

The device for indoor air purification and sterilization according to the present invention is characterized in that contaminated substances and bad smells are decomposed by exciting the air with the aid of arc discharge, thus sterilizing germs, and the magnetic field is applied to the excited air, thus maintaining the excited state, so the air purification and sterilization efficiencies are greatly enhanced.

The device for indoor air purification and sterilization according to the present invention is characterized in that noises occurring during arc discharge are reduced by a muffler, and the ozone is removed by an ozone elimination filter, and static electricity is eliminated by a static electricity elimination metallic filter, so the present invention can be well adapted to the purification and sterilization of the indoor space where people dwell.

The features and advantages of the present invention might be more clarified with the following detailed descriptions. The terms or words used in the specification and claims are not deemed to be interpreted in a conventional and dictionary way, but deemed to be interpreted as the meaning and concept well matching with the technical concepts of the present invention based on the principle that the inventor can well defines the concepts of the terms for the purpose of describing his invention in the best way.

Figure 1:
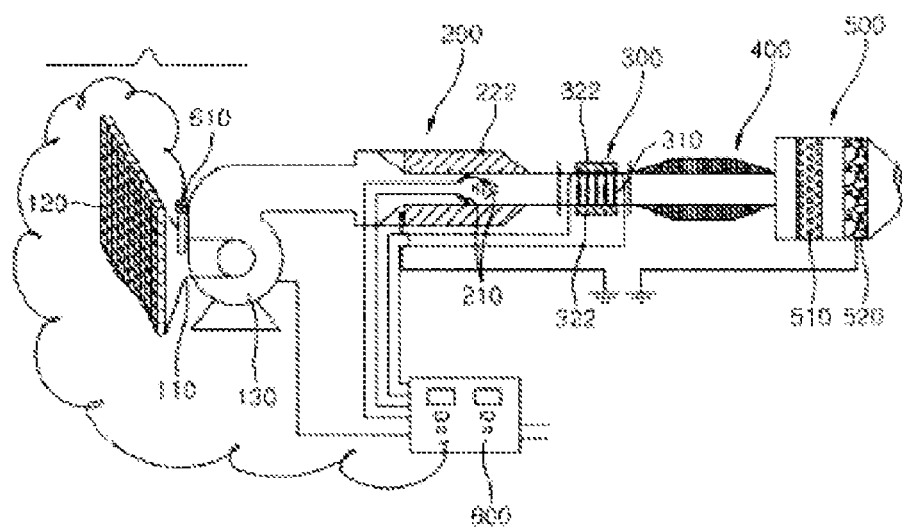
FIG. 1 is a view illustrating the whole system configuration of a device for indoor air purification and sterilization according to the present invention.

<Descriptions of reference numerals of key elements in the drawings>

| | |
|---|---|
| 110: suction tube | 120: dust elimination pretreatment filter |
| 130: air pump | 200: arc discharge part |
| 210: arc discharge unit | 220: discharge support tube |
| 221: titanium dioxide catalyst layer | 222: electromagnetic wave shield layer |
| 300: magnetic field process part | 310: induction coil |
| 320: induction coil support tube | 321: magnetic layer |
| 322: permanent magnet | 400: muffler |
| 410: muffler pipe | 420: sound absorption material |
| 430: noise reduction baffle | 500: exhaust tube |
| 510: ozone elimination filter | 520: static electricity elimination metallic filter |
| 600: control part | 610: contamination detection sensor |

MODES FOR CARRYING OUT THE INVENTION

The present invention is directed to providing a device for indoor air purification and sterilization which is characterized in that contaminated substances and bad smells are decomposed and sterilized by exciting the contaminated gases which are contaminated indoor air by means of arc discharge, and the excited state is maintained by applying magnetic field, and the purification efficiency is enhanced by extending the contract duration time between arc-activated molecules and contaminated substances, and the noises, ozone and static electricity generating due to the arc discharge are eliminated or reduced, thus well being applied to the purification and sterilization of the indoor air.

The device for indoor air purification and sterilization according to the present invention will be described with reference to the accompanying drawings.

Figure 2:
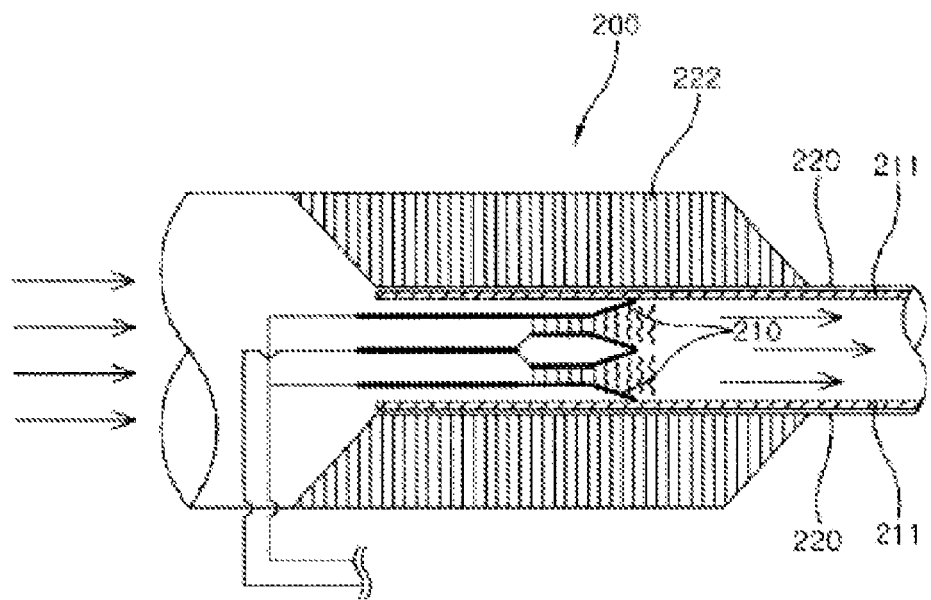
FIG. 2 is a cross sectional view illustrating an arc discharge part of a device for indoor air purification and sterilization according to the present invention.
Figure 3:
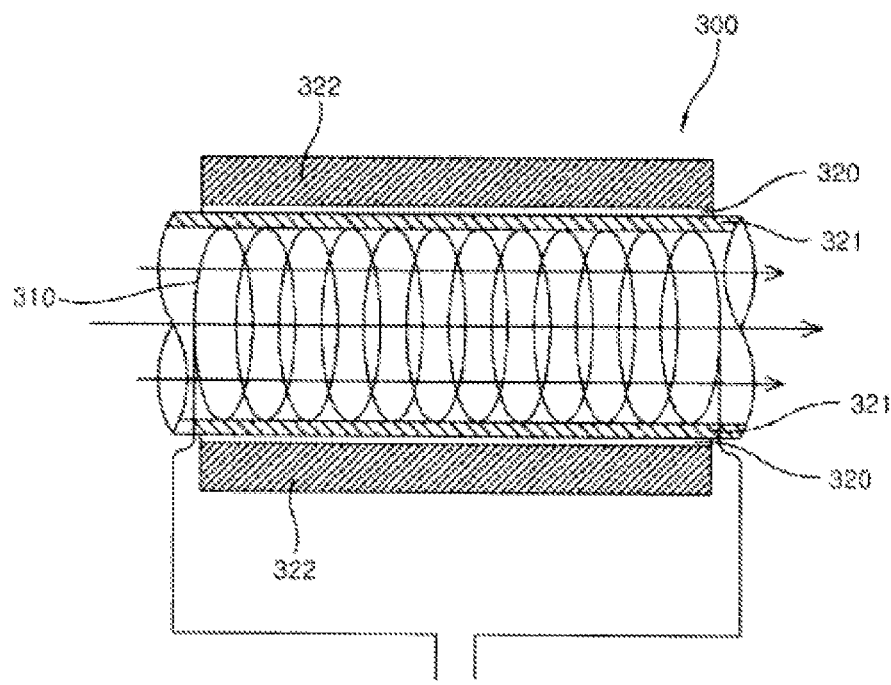
FIG. 3 is a cross sectional view illustrating a magnetic field process part of a device for indoor air purification and sterilization according to the present invention.
Figure 4:
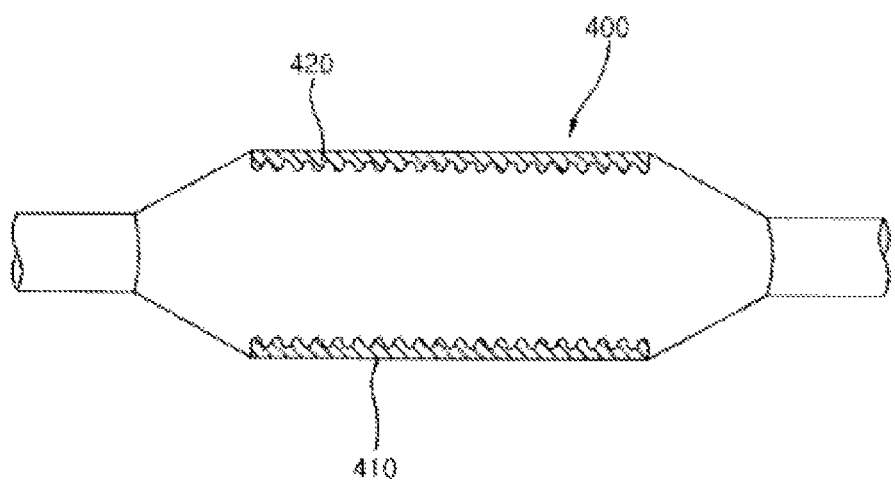
FIG. 4 is a view of a first example of a muffler of a device for indoor air purification and sterilization according to the present invention.
Figure 5:
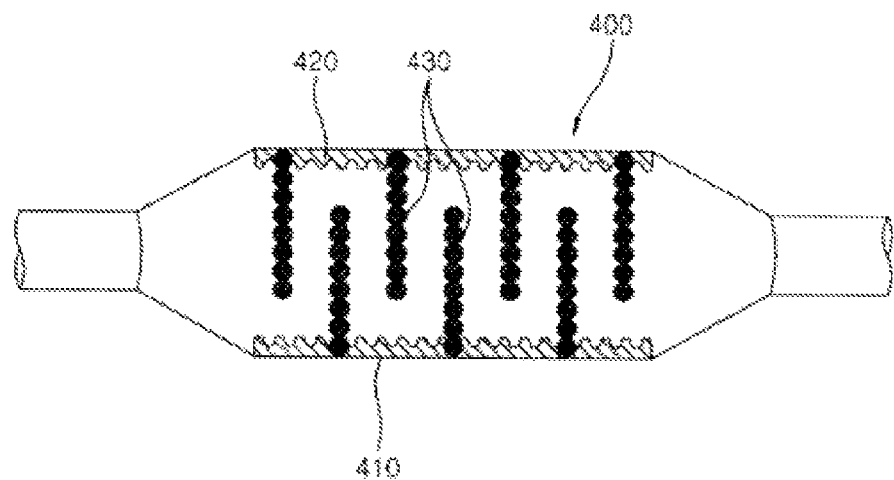
FIG. 5 is a view of a second example of a muffler of a device for indoor air purification and sterilization according to the present invention.
Figure 6:
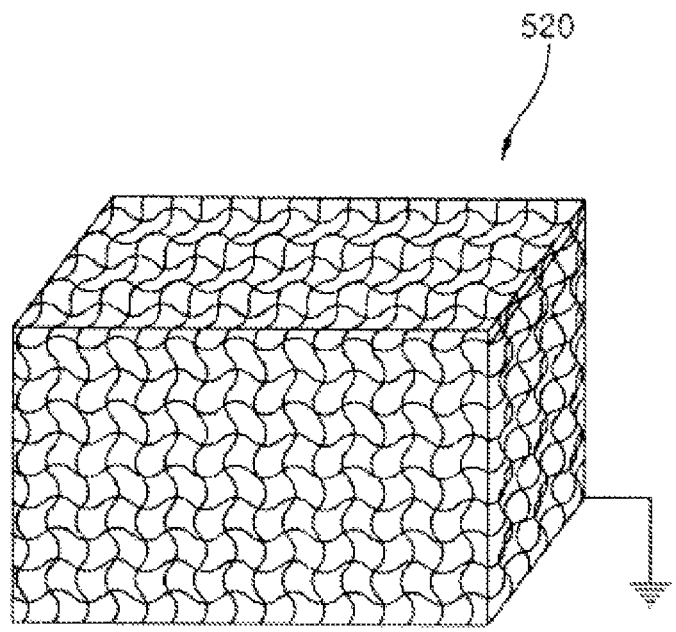
FIG. 6 is a view of an example of a static electricity elimination metallic filter of a muffler of a device for indoor air purification and sterilization according to the present invention.

FIG. 1 is a view illustrating the whole system configuration of a device for indoor air purification and sterilization according to the present invention. FIG. 2 is a cross sectional view illustrating an arc discharge part of a device for indoor air purification and sterilization according to the present invention. FIG. 3 is a cross sectional view illustrating a magnetic field process part of a device for indoor air purification and sterilization according to the present invention. FIG. 4 is a view of a first example of a muffler of a device for indoor air purification and sterilization according to the present invention. FIG. 5 is a view of a second example of a muffler of a device for indoor air purification and sterilization according to the present invention. FIG. 6 is a view of an example of a static electricity elimination metallic filter of a muffler of a device for indoor air purification and sterilization according to the present invention.

Referring to FIGS. 1 through 6, the device for indoor air purification and sterilization according to the present invention is characterized in that a suction tube is disposed at one side of a housing.

There is provided a housing having a certain volume enough to accommodate key elements of a device for indoor air purification and sterilization. A suction tube 110 is disposed at one side of the housing for the purpose of sucking contaminated gases. As the contaminated gases sucked into the suction tube 110 are excited by means of arc discharge, thus decomposing and sterilizing the contaminated substances and bad smells. As the magnetic field is applied to the excited air, the excited state can be maintained, and the contact duration time between the arc-activated molecules and the contaminated substances can be extended, thus enhancing purification efficiency.

There is provided a contamination detection sensor 610 for the purpose of measuring the contaminated air sucked into the suction tube 110, thus measuring the kinds and contents of the contained contaminated substances. A control part 600 connected to the contamination detection sensor 610 is disposed in the interior of the device for indoor air purification and sterilization. The control part 600 properly controls for the operations of the arc discharge 210 of the arc discharge part and the induction coil 310 of the magnetic field process part to be optimum depending on a result of the measurement of the contaminated substances measured by the contamination detection sensor 610 disposed at the suction tube 110, thus consequently enhancing the air purification and sterilization efficiencies. At the same time, the energy consumption can be reduced by inhibiting the unnecessary operations of the arc discharge unit 210 and the induction coil 310.

The device for indoor air purification and sterilization according to the present invention comprises a dust elimination pretreatment filter disposed at the suction tube.

The indoor air contains a variety of physically, chemically and biologically different contamination substances each of which also contains dusts. When the contaminated gas with dusts is sucked into the suction tube 110, the dusts of the contaminated gas interferes with arc discharge, so the contaminated gases are not fully excited, and the electrodes might be damaged due to the dusts.

For the purpose of resolving the above problems, the present invention provide a dust elimination pretreatment filter 120 at the entrance or interior of the suction tube 110, thus filtering the contaminated gases and consequently separating the dusts. The contaminated gases are filtered by the dust elimination pretreatment filter 120 engaged at the suction tube 110, thus separating the dusts. Since the contaminated gases from which the dusts are separated are transferred to the arc discharge part 200 and are excited by means of arc discharge, the damages of the electrodes and the decrease in the discharge efficiency due to the dusts do not occur.

The device for indoor air purification and sterilization according to the present invention is directed to providing an air pump or an air suction fan which is disposed near the dust elimination pretreatment filter.

There is provided an air pump 130 or an air suction fan near the dust elimination pretreatment filter 120 in the interior of the suction tube 110 for the purpose of sucking indoor air and transferring toward the arc discharge part 200. The air pump 130 or the air suction fan disposed in the interior of the suction tube 110 serves to provide the pressures to be used to suck the contaminated gases into the device for indoor air purification and sterilization and to discharge the air purified and sterilized by the device for indoor air purification and sterilization into the indoor space.

The device for indoor air purification and sterilization according to the present invention comprises an arc discharge unit exciting the contaminated gases sucked by the air pump or the air suction fan, a titanium dioxide catalyst layer at the inner surface of the discharge support tube accommodating the arc discharge part, and an arc discharge part on an outer surface of which an electromagnetic wave shielding layer is formed.

There is provided an arc discharge part 200 which is connected with the suction tube 110 and decomposes and sterilizes the contaminated substances contained in the contaminated gases in such a way that a high voltage is applied to the contaminated gases transferred by means of the air pump 130 or the air suction fan, thus exciting the contaminated gases to become a high energy state and they are oxidized with the aid of titanium dioxide.

The arc discharge part 200 comprises an arc discharge unit 210 consisting of a plurality of arc discharge electrodes for the purpose of arc discharging for the contaminated gases to excite and forming an arc discharge band, an a metallic discharge support tube 220 accommodating the arc discharge unit 210. A titanium dioxide catalyst having a strong oxidation function with respect to the contaminated substances is coated on an inner surface of the discharge support tube 220, thus forming a titanium dioxide catalyst layer 221. An electromagnetic wave shielding layer 222 made from a known electromagnetic wave shielding material is formed at an outer surface of the discharge support tube 220.

The arc discharge unit 210 accommodated in the discharge support tube 220 of the arc discharge part is formed of a plurality of arc discharge electrodes. A discharge occurs between the arc discharge electrodes of the arc discharge unit 210 to which a high voltage is applied, thus generating high energy electrons. As the generated high energy electrons are condensed, so an arc discharge band is formed between the arc discharge electrodes.

The contaminated gases introduced into the arc discharge part 200 are converted into the excited states by means of high energy electrons as they pass through the arc discharge band between the arc discharge electrodes of the arc discharge unit 210, so the contaminated substances contained in the contaminated gases are decomposed, and bacteria are sterilized. In details, the arc active molecules such as active oxygen, active nitrogen, hydrogen atoms, $CH_3$ radicals, OH radicals, etc. each having a very strong oxidation force are produced from the contaminated gases by means of high energy electrons generated as the arc is discharged at the arc discharge electrodes of the arc discharge unit 210, and the thusly produced arc active molecular come into direct contact with the contaminated substances of the contaminated gases, thus first oxidizing the contaminated substances and converting into the compounds which are not harmful to human bodies.

It is inevitable that visible light, ultraviolet ray, electromagnetic waves harmful to human bodies, noises of 85-88 dB, ozone and static electricity are produced during the procedure that the contaminated substances are oxidized and are converted into the compounds not harmful to human bodies as the arc active molecules generated by means of the arc discharge of the arc discharge unit 210 come into direct contact with the contaminated substances of the contaminated gases. Unless the visible light, ultraviolet ray, electromagnetic waves, noises, ozone and static electricity are fully decreased or eliminated, it is hard to apply to the device for indoor air purification and sterilization.

A titanium dioxide catalyst layer 221 having a function converting the contaminated substances into the compounds not harmful to human bodies is provided at the arc discharge part 200 for the purpose of ensuring that the visible light and ultraviolet ray generating from the arc discharge of the arc discharge unit 210 are recycled when second oxidizing the contaminated substances of the contaminated gases. In more details, a titanium dioxide catalyst layer 221 with a certain thickness is formed by coating a titanium dioxide catalyst, which has an excellent oxidation function with the aid of a visible light and a ultraviolet ray, on an inner surface of the discharge support tube 220 accommodating the arc discharge unit 210 of the arc discharge part 200. The titanium dioxide catalyst layer 221 formed at an inner surface of the discharge support tube 220 is characterized in that oxidation function is activated by means of a visible light and a ultraviolet ray generating by means of an arc discharge of the arc discharge unit 210, and the contaminated substances of the contaminated gases are second oxidized by means of the oxidation function of the titanium dioxide catalyst layer 221 and are converted into the compounds which are not harmful to human bodies.

The electromagnetic waves generating by means of an arc discharge of the arc discharge unit 210 have a function of a little expediting the decomposition of the contaminated substances contained in the contaminated gas, but are very harmful to human bodies. In order to resolve the above problems, there is provided an electromagnetic wave shielding layer 222 formed of electromagnetic wave shielding materials at an outer surface of the discharge support tube 220 accommodating the arc discharge unit 210 for the purpose of shielding the electromagnetic waves generating from the arc discharge of the arc discharge unit 210. The electromagnetic wave shielding material shielding the electromagnetic waves from the electronic instruments is classified into a reflection type electromagnetic wave shielding material made from a conductive material and having a function of reflecting electromagnetic waves, and an absorption type electromagnetic wave shielding material made from a semi-conductive material and having a function of absorbing electromagnetic waves. The present invention is directed to using a reflection type electromagnetic wave shielding material having a function of reflecting electromagnetic waves. It is preferred that an electromagnetic wave shielding layer 222 is formed at an outer surface of the discharge support tube 220 for thereby reflecting electromagnetic waves for the purpose of ensuring that the electromagnetic waves due to the arc discharge of the arc discharge unit 210 is reflected and at the same time the electromagnetic waves are prevented from going out to the outside of the arc discharge part 200, which enables the reflected electromagnetic waves to expedite the decompositions of the contaminated substances.

A reflection type electromagnetic wave shielding material selected from the group consisting of a conductive carbon and a carbon fiber non-woven cloth each having an excellent electromagnetic wave reflection and shielding function and a certain flexibility is coated on an outer surface of the discharge support tube 200 of the arc discharge part, thus forming an electromagnetic wave shielding layer 222 with a certain thickness. The electromagnetic wave shielding layer 222 formed at an outer surface of the discharge support tube 200 serves to reflect the electromagnetic wave from the arc discharge of the arc discharge unit 210 and shields the same from going out to the outside of the arc discharge part 200, thus protecting the human bodies from the electromagnetic waves, and at the same time the reflected electromagnetic waves help expedite the decomposition of the contaminated substances in the interior of the arc discharge part 200, thus enhancing the elimination efficiency of the contaminated substances.

In addition, the noises of 85-88 dB due to the arc discharge of the arc discharge unit 210 is a lot reduced by means of the muffler 400, which will be described later, and the ozone is decomposed and eliminated by means of the ozone elimination filter 510 which will be described later. Since the static electricity is eliminated as it is grounded by the static electricity elimination metallic filter 520, so the noises, ozone and static electricity do not affect the people who stay indoors.

The device for indoor air purification and sterilization according to the present invention comprises a magnetic field process part having an induction coil maintaining an excited state by applying magnetic field to the gas transferred from the arc discharge part. A magnetic layer is formed at an inner surface of the induction coil support tube accommodating the induction coil. An outer surface of the magnetic field process part is covered by the permanent magnet.

There are effects that the contaminated gases are converted into excited states by means of high energy electrons coming from the arc discharge electrodes of the arc discharge unit 210, thus decomposing the contaminated substances and sterilizing bacteria, but actually speaking, since the arc activated molecules generating due to the arc very randomly move, the contact duration time between the arc activated molecules and the contaminated substances is short, and the contact efficacy is low. Since the life span of the arc activated molecules is short, and the excited states are not fully maintained to the extent that the contaminated substances are properly decomposed, it is hard to expect the effects that the contaminated gases are fully purified and sterilized while affecting the human bodies.

When the magnetic field is applied to the arc activated molecules produced by means of the arc discharge, the life span of the arc activated molecules is largely extended, and the excited states of the contaminated gas including the arc activated molecules can be maintained long as the extended life span.

With the above features, the present invention is directed to providing a magnetic field process part 300 which applies magnetic fields for the purpose of extending a contact duration time between the arc activated molecules contained in the contaminated gases and the contaminated substances and enhancing the contact efficiency in such a way that the excited states of the contaminated gases excited by means of the arc discharge in the arc discharge part 200 are extended, and the contaminated gases the excited states of which are extended are arranged and guides in a specific direction.

The magnetic field process part 300 comprises an induction coil 310 which applies a magnetic field to the excited contaminated gas and guides in a specific direction with the aid of an electric bipolar moment, and a metallic induction coil support tube 320 through which the magnetic field covering the induction coil 310 passes. A magnetic layer 321 coated with a magnetic powder is formed at an inner surface of the induction coil support tube 320, and a permanent magnet 322 covers an outer surface of the induction coil support tube 320.

The induction coil 310 disposed in the induction coil support tube 320 of the magnetic field process part applies a solenoid magnetic field to the contaminated gases excited by means of the arc discharge in the arc discharge part 200, thus extending the life span of the arc activated molecules, which helps maintain the excited states. It helps arrange the excited contaminated gases and guide the same in a specific direction with the aid of the bipolar moment, so the contact duration time between the arc activated molecules contained in the contaminated gases and the contaminated substances.

The magnetic layer 321 formed at an inner surface of the induction coil support tube 320 and the permanent magnet 322 disposed at an outer surface of the same server to apply magnetic fields to the excited contaminated gases, thus largely extending the life span of the arc activated molecules contained in the contaminated gases. So, the excited states of the contaminated gases containing the arc activated molecules are maintained long as the extended life span.

The excited contaminated gases are arranged by means of the solenoid magnetic field applied from the induction coil 310 and are guided in a specific direction by means of the bipolar moment, so the contact duration time between the arc activated molecules contained in the contaminated gas and the contaminated substances is extended for the purpose of ensuring that the life span of the arc activated molecules contained in the contaminated gases is largely extended by means of the magnetic fields supplied from the magnetic layer 321 and the permanent magnet 322 of the induction coil support tube 320, and the excited states of the contaminated gases containing the arc activated molecules are extended long as the extended life span, thus fully purifying and sterilizing the contaminated gases.

The device for indoor air purification and sterilization according to the present invention comprises a muffler which is connected with the magnetic field process part and is formed of a sound absorption material at an inner surface of the muffler pipe 410 or a plurality of noise reduction baffles.

When the arc discharge unit 210 arc-discharges, noise of 85-88 dB occurs, which noises might cause uneasiness to people staying in the indoor space. Unless the noises generating when the arc discharge unit 210 arc-discharges is largely reduced, it is hard to be applied to the device for indoor air purification and sterilization.

The present invention comprises a muffler 400 which is connected with the magnetic field process part 300 and absorbs or reduce the noises generating when the arc discharge unit 210 arc-discharges.

More specifically, the muffler 400 is configured in such a way that a sound absorption material 420 is formed at an inner surface of the muffler pipe 410 connected with the magnetic field process unit 300 or a plurality of noise reduction baffles 430 are formed. The muffler 400 is characterized in that the noises generating when the arc discharge unit 210 arc-discharges are absorbed or reduced by the sound absorption material 420. The noises might be released or reduced by means of a plurality of noise reduction baffles 430.

The device for indoor air purification and sterilization according to the present invention comprises an ozone elimination filter which is disposed in the interior of the exhaust tube connected with the muffler and is configured in such a way that at least one ozone decomposition catalyst selected form the group consisting of $MnO_2$, CuO and zeolite is loaded.

Ozone is produced from the arc discharge band when the arc discharge unit 210 arc-discharges. The ozone severely affects the people staying in the indoor space. Unless the ozone generating when the arc discharge unit 210 arc-discharges is not removed, it is hard to apply to the device for indoor air purification and sterilization.

The present invention comprises an exhaust tube 500 which is connected with the muffler 400 for thereby exhausting the purified and sterilized air, and an ozone elimination filter 510 decomposing and eliminating the ozone from the purified and sterilized air in the interior of the exhaust tube 500.

More specifically, in the interiors of the exhaust tube 500 connected with the muffler 400 is provided an ozone elimination filter which is made from a porous carrier adapted as a base bacterial and allowing air to pass and is characterized in that at least one ozone decomposition catalyst is loaded in the porous carrier, which ozone decomposition catalyst is selected from the group consisting of $MnO_2$, CuO and zeolite. The ozone elimination filter 510 disposed in the exhaust tube 500 is configured to decompose ozone which is provided when the arc discharge unit 210 arc-discharges.

The device for indoor air purification and sterilization according to the present invention comprises a static electricity elimination metallic filter which is disposed near the ozone elimination filter and is made from copper or a stainless steel material.

Static electricity generally occurs from the arc discharge band when the arc discharge unit 210 arc-discharges. Since the static electricity gives bad effects to the health of people staying in the indoor space, unless the static electricity generating when the arc charge unit 210 arc-charges, it is hard to be applied to the device for indoor air purification and sterilization.

In the present invention, there is provided a static electricity elimination metallic filter 520 near the ozone elimination filter 510 in the interior of the exhaust tube 500 connected with the muffler 400 for the purpose of collecting and grounding and eliminating the static electricity from the purified and sterilized air.

In details, there is provided a static electricity elimination metallic filter 520 in the interior of the exhaust tube 500 connected with the muffler 400. The static electricity elimination metallic filter 520 is made from copper or a stainless steel material and is grounded. The static electricity elimination metallic filter 520 disposed in the interior of the exhaust tube 500 serves to eliminate by collecting and grounding the static electricity contained in the purified and sterilized air.

There might be provided a static electricity elimination metallic filter 520 which configured in a two-dimensional structure with a copper wire or a stainless steel wire, thus collecting and grounding and eliminating the static electricity contained in the air while allowing the air to pass. In the present invention, it is preferred that there is provided a static electricity elimination metallic filter 520 which is configured in such a manner that a copper wire or a stainless steel wire is arranged in a three-dimensional structure or is tangled in a three-dimensional structure for the purpose of ensuring that the contact area and the contact duration time between the static electricity elimination metallic filter 520 and the purified and sterilized air can largely increase, thus significantly enhancing the static electricity elimination effects.

The air from which the static electricity is eliminated by means of the static electricity elimination metallic filter 520 is discharged into the indoor space via the exhaust tube 500.

The device for indoor air purification and sterilization according to the present invention is directed to decomposing and sterilizing the contaminated substances and bad smells by exciting the indoor air with the aid of arc discharge, and the excited states are maintained by applying magnetic field, and the air purification and sterilization efficiencies can be significantly enhanced in such a way to extend the contact duration time between the arc activate molecules and the contaminated substances.

The device for indoor air purification and sterilization according to the present invention makes it possible to reduce the noises occurring during the arc discharge with the aid of the muffler, and the ozone is eliminated by the ozone elimination filter, and the static electricity is eliminated by the static electricity elimination metallic filter, so it can be well applied to the people-residing indoor air purification and sterilization.

As described above, the preferred embodiments of the present invention has been described, but the present invention is not limited to the above embodiments, and it is obvious that an ordinary person skilled in the art can modify the present invention without departing from the concepts of the present invention.

The invention claimed is:

1. A device for indoor air purification and sterilization, comprising:
    a suction tube which is disposed at one side of a housing;
    a dust elimination pretreatment filter which is formed at the suction tube;
    an air pump which is disposed near the dust elimination pretreatment filter;
    an arc discharge part which has an arc discharge unit for exciting the contaminated gases sucked by means of the air pump, a titanium dioxide ($TiO_2$) formed at an inner surface of a discharge support tube accommodating the arc discharge unit, and an electromagnetic wave shielding layer formed at an outer surface;

a magnetic field process part which has an induction coil for the purpose of maintaining an excited state by applying a magnetic field to the gas from the arc discharge part and a magnetic layer formed at an inner surface of the induction coil support tube accommodating the induction coil, with the outer surface of the magnetic field process part being covered by means of permanent magnets;

a muffler which is connected with the magnetic field process part and has a sound absorption material on its inner surface or has a plurality of noise reduction baffles;

an ozone elimination filter which is disposed in the interior of an exhaust tube connected with the muffler and is configured in such a manner that at least one ozone decomposition catalyst selected from the group consisting of $MnO_2$, CuO and zeolite is loaded at a porous carrier; and a static electricity elimination metallic filter which is disposed near the ozone elimination filter and is made from copper or a stainless steel material and is grounded.

2. A device for indoor air purification and sterilization according to claim 1, to wherein an electromagnetic wave shielding layer is formed in such a way that a reflection type electromagnetic wave shielding material selected from the group consisting of a conductive carbon and a carbon fiber non-woven cloth is coated on an outer surface of the discharge support tube of the arc discharge part.

3. A device for indoor air purification and sterilization according to claim 1, wherein said static electricity elimination metallic filter disposed in the exhaust tube is configured in such a way that a copper wire or a stainless steel wire is arranged in a three-dimensional structure or is tangled in a three-dimensional structure.

4. A device for indoor air purification and sterilization according to claim 1, further comprising:
    a contamination detection sensor formed to measure a contaminated substance of a contaminated gas in the suction tube;
    an arc discharge unit which belongs to an arc discharge part and operates based on a result of the measurement of the contaminated substances measured by the contamination detection sensor; and
    a control part which controls the operations of the induction coil of the magnetic field process part.

* * * * *